United States Patent [19]

Mommer

[11] Patent Number: 4,576,593
[45] Date of Patent: Mar. 18, 1986

[54] DOSING DEVICE FOR INFUSION OR TRANSFUSION OF FLUIDS

[75] Inventor: Heinrich Mommer, Stolberg, Fed. Rep. of Germany

[73] Assignees: M. Faensen; Iphas Pharma-Verpackung, both of Fed. Rep. of Germany

[21] Appl. No.: 577,967

[22] Filed: Feb. 8, 1984

[30] Foreign Application Priority Data

Feb. 11, 1983 [DE] Fed. Rep. of Germany ....... 3304831

[51] Int. Cl.$^4$ ................................................ A01F 2/80
[52] U.S. Cl. ..................................... 604/250; 604/86; 604/34; 251/4; 251/7; 251/8
[58] Field of Search ............... 604/250, 34, 86; 251/4, 251/7, 8

[56] References Cited

U.S. PATENT DOCUMENTS

| | | | |
|---|---|---|---|
| 3,329,391 | 7/1967 | Deane | 604/250 |
| 3,460,526 | 8/1969 | McKirdy et al. | 604/250 |
| 3,759,483 | 9/1973 | Baxter | 251/7 |
| 3,831,600 | 8/1974 | Yum et al. | 604/250 |
| 3,861,388 | 1/1975 | Vaughn | 604/86 |
| 3,948,477 | 4/1976 | Lample | 604/250 |
| 3,960,149 | 6/1976 | Bujan | 604/250 |
| 4,410,164 | 10/1983 | Kamen | 604/34 |

Primary Examiner—R. L. Andrews
Attorney, Agent, or Firm—Birch, Stewart, Kolasch & Birch

[57] ABSTRACT

The invention relates to a dosing device for fluids used in infusion or transfusion systems comprising a flexible fluid line transversing a housing to compress the fluid line. The device comprises a housing and an elastomeric tubular element having leading and trailing sections which traverses said housing to interconnect respective ends of said fluid line. The tubular element comprises a thicker portion between the leading and trailing sections whereby the thicker portion protects against longitudinal displacement of the housing. A pressing element engages the tubular element outside the region of the thicker portion.

11 Claims, 9 Drawing Figures

DOSING DEVICE FOR INFUSION OR TRANSFUSION OF FLUIDS

BACKGROUND OF THE INVENTION

The invention relates to a dosing device for fluids used in infusion or transfusion systems comprising a flexible fluid line transversing a housing and a pressure element supported in the housing to compress the fluid line.

To perform infusions or transfusions, a reservoir containing the infusion or transfusion fluid and having a downwardly directed aperture, as well as a connected fluid line, is suspended as high as is considered necessary to ensure that the fluid pressure in the line is higher than the vein pressure of the patient. The fluid is delivered first to an intermediate container in the fluid line and then from there to the patient. Due to the different marginal conditions, e.g. the vein pressure of the patient, the viscosity of the fluid and the varying filling height of the fluid container and due to the fluid dosages determined therapeutically, it is necessary to accurately adjust the rate of flow of the fluid.

There have been known dosing means of the above mentioned type comprising a fluid line extending through a housing and a clamping element which consists of a roller guided in the housing and pressing on the hose cross section (DE-OS No. 26 37 495). The dosage amount usually determined by the number of fluid drops dripping per unit of time into the intermediate container cannot be kept constant for a long period with such a device because the PVC-hoses usually applied may deform due to their creep tendency (cold flow property). Problems will develop above all if the dosage amount needs to be increased leading to a longer compression of the fluid line than previously considered necessary, because the tough-elastic relaxation behavior present as a result of hysteresis of the plastic line inhibits a quick recovery of the original line cross section. Hence, even with constant adjustment a constant dosage cannot be realized with such dosing devices.

There has also been provided a dosing means comprising a housing and a substantially cylindrical valve chamber provided therein, with two connecting pieces having a respective channel and projecting radially from the housing or valve chamber in opposite directions, and a plug rotatable with a handle and sealingly disposed in the valve chamber. In the jacket surface of the plug, a passage is provided which when subjected to the rotary position of the plug admits, between the connecting pieces, flow cross sections of different dimensions. (DE-OS No. 27 35 955). Such dosing means are involved with a considerable constructional expenditure to ensure a safe sealing of the dosing means against air access.

Therefore, it is an object of the present invention to provide a fluid dosing means for infusion or transfusion devices which will overcome the above noted and other disadvantages.

It is another object of the present invention to provide a dosing means which permits an accurate, time-constant and reproducibly adjustable dosing of fluids.

SUMMARY OF THE INVENTION

The foregoing objects and others are accomplished in accordance with the present invention by providing a fluid line which contains inside a housing a hose or tubular element of highly flexible elastomeric material. The fluid line may be made of suitable plastics in the conventional manner. The elastomeric hose portion provided therein at a suitable site and surrounded by a housing forms in common with the latter, together with a pressure element and an adjusting means, the respective dosing unit. The hose portion has a high flexibility and restoring force thus imparting to the cross sectional face of the hose portion the tendency of returning to its original relaxed condition, this being controlled by the adjusting element, which is a pressing member in the instant case. A change in the position of the pressing element will cause an immediate change in the flow at the specific cross section of the hose portion, including the withdrawal of the pressing element. The resultant dosing accuracy is very high allowing the dripping rate of the fluid to be maintained substantially constant in time and reproducible by adjustment. The dosing means of the present invention ensures considerable air-tightness because the device controlling the flow, i.e. the hose portion in the instant case, is made of one piece. This is a very important safety feature with respect to intra-venous infusion and transfusion devices. The dosing means may also be produced at a reasonable price. The housing is an injection molded part made of one piece. Moreover, the housing, the adjusting means and the pressure element need not be sterilized because only the hose portion will come into contact with the infusion or transfusion fluid, so that the cost in regard to the sterilization of the dosing means and the risk of imperfect sterilization are avoided.

According to one preferred embodiment of the present invention, part of the longitudinal hose portion is thicker than the remaining portion with longitudinal displacement being protected against by the presence of the thicker part in the housing, with the pressure element engaging the hose portion outside the thicker region. Due to the shape of the hose portion, the position of the housing is exactly fixed. It is also quite advantageous that the hose portion can be readily obtained in the market as an injection molded part thus doing away with the need for special elements. In the dosing means of the present invention, the hose portion may be also used for the injection of additional medicaments or fluids by means of a syringe. The air-tightness of the dosing means is also ensured upon the puncturing and removing of a needle cannula because the hose or tubular portion is made of a highly flexible material. Due to the thicker part of the hose portion, a larger clearance in the cavity thereof is guaranteed when taking into consideration the depth of penetration of the needle cannula, thus increasing the safety of the device.

In accordance with the above discussion, it is apparent that the utility of the hose portion is of a dual nature. On the one hand, medicaments may be injected, preferably via the thicker portion, and on the other hand, in connection with the pressing element, the rate of flow of the infusion or transfusion fluid is reliably and accurately administered. These two objects have been achieved heretofore only with the use of two hose sections.

Another preferred embodiment of the present invention is characterized in that the pressing function is conducted by the pressing element transverse to the longitudinal direction of the hose portion and that the front side of the pressing element pressing against the hose portion is inclined relative to the direction of movement thereof. Due to such an asymmetrical deformation of the hose portion, the latter can be clamped successively from one side thus preventing it from retaining a deformation in another cross sectional shape, in spite of its elasticity, e.g. in the form of an eight, or from changing its cross sectional shape suddenly. This ensures a particularly accurate, reproducibly adjustable dosage.

According to another embodiment, the present invention is characterized in that the housing includes a puncture channel for a needle cannula. By this means, the needle cannula is introduced at a specific location of the hose portion.

In another preferred embodiment, the invention is characterized in that the puncture cannula extends at an acute angle relative to the longitudinal axis of the hose portion to maintain the most favorable puncture angle in accordance with the guidance of the needle cannula. The injection will be effected more safely because a maximum free path is obtained for the point of the needle in the hose portion. This is important if, in cases of emergency, the injection must be made very quickly, because the needle point can be positioned more easily and more safely in the hose cross section and the second hose wall cannot be perforated by too deep a puncture, whereby the injection fluid would not get into the blood circulation.

Provided as an advantageous embodiment of the invention, the pressure element is movable via a manually adjustable, self-locking adjusting means which, preferably, may consist of a threaded spindle positioned in the housing. Subject to the thread pitch, the spindle allows for the injection of a particularly accurate and reproducible dosage. The adjusting means may be provided with a detachable handle portion to increase safety against incidental or undesired adjustment of the dosing means, because it cannot be set when the handle portion is removed.

The preferred embodiments of the present invention will now be explained in more detail with reference to the accompanying drawings which are intended to illustrate but not limit the scope of the present invention.

DETAILED DESCRIPTION

Figure 1:
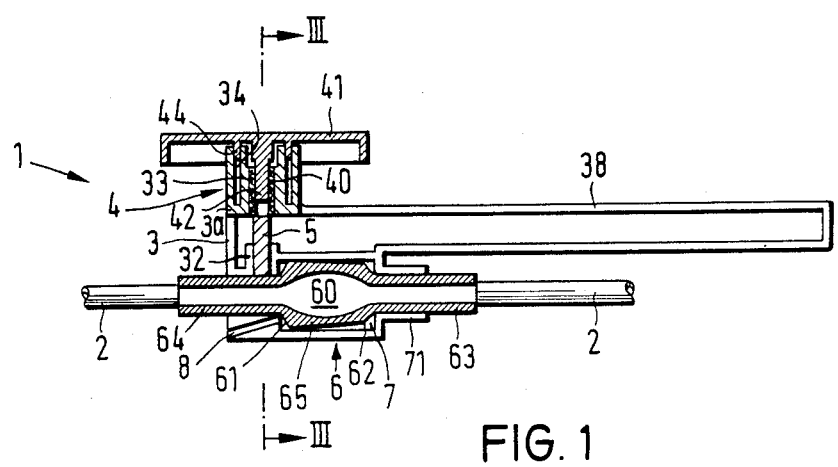
FIG. 1 is a longitudinal sectional view of a dosing means comprising a threaded spindle as an adjusting device.
Figure 2:
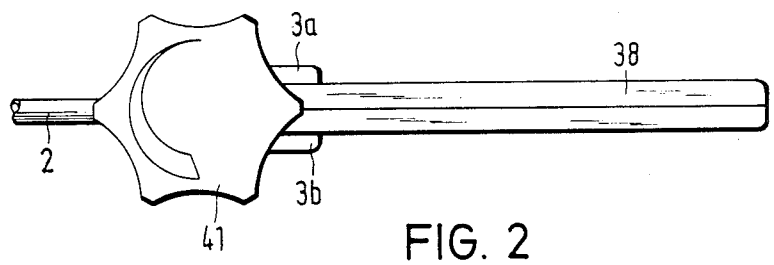
FIG. 2 is a plan view of the dosing means of FIG. 1.

The embodiments shown in FIGS. 1 to 9 relate to a dosing means provided in an infusion- or transfusion device. Therefore, the dosing means 1 in a fluid line 2 is disposed between an infusion container and a patient. It comprises a housing 3 to receive an adjusting device 4, a pressing element 5 and a hose portion 6 inserted into the fluid line 2.

The hose portion 6 is a injection valve of a highly-elastic elastomer which is normally interconnected in a pvc-fluid line 2 to permit injection, for instance, of medicaments by infusion or transfusion. To connect it to the conventional pvc-fluid line 2, the two ends of the flexible hose portion 6 tightly overlap the ends of the fluid conduit 2. It is also possible to use connecting pieces such as employed in conventional infusion devices. The central region of the hose portion 6 preferably contains a thicker part 65, both ends of which are formed as annular shoulders reduced to cylindrical hose sections 63 and 64 which are somewhat larger in cross section than the cross section of the fluid line 2. The thick part 65 fixes the position of the total dosing means 1 at a specific point in the fluid line 2. Moreover, the wall thickness may be reinforced accordingly. This is important if the hose portion 6, specifically the thicker portion 65, in the dosing means 1 is also used for injection purposes. The thicker part 65 ensures a free path as long as possible to the cavity 60 of the hose portion 6 for the puncture of a needle cannula (not shown). The highly elastic material of the hose portion 6 is responsible for the immediate closing of the puncture hole upon the piercing of the wall of the hose portion 6 by a needle cannula and upon the extraction of the needle cannula.

Figure 3:
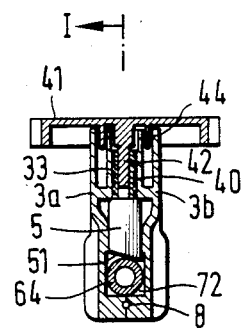
FIG. 3 is a sectional view along the line III—III of FIG. 1.
Figure 4:
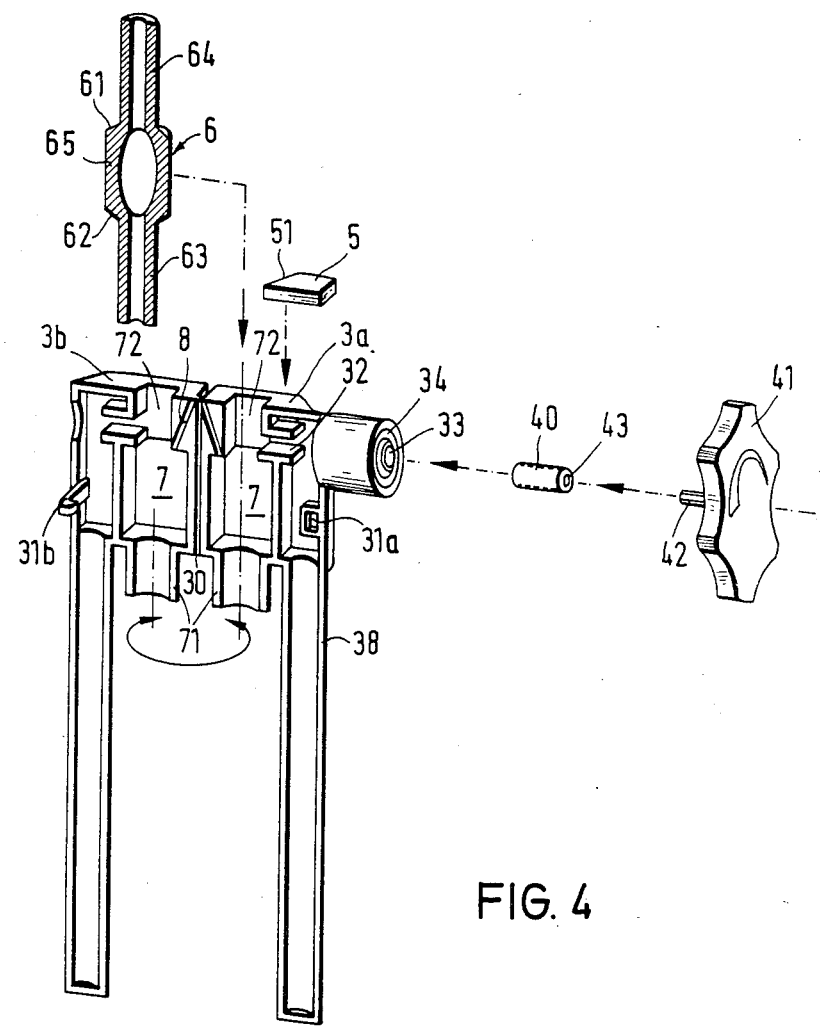
FIG. 4 is an exploded perspective view of the dosing means of FIG. 1 in which the housing halves are opened.
Figure 5:
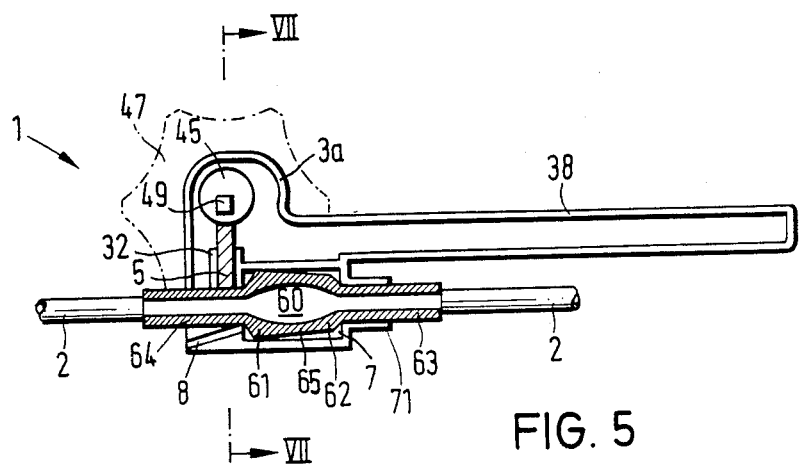
FIG. 5 is a longitudinal sectional view of a dosing means comprising an eccentric as an adjusting device.
Figure 6:
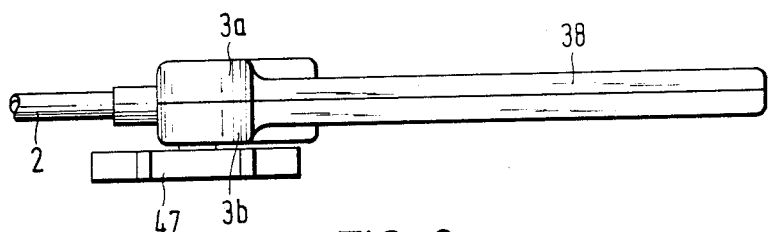
FIG. 6 is a plan view of the dosing means of FIG. 5.
Figure 7:
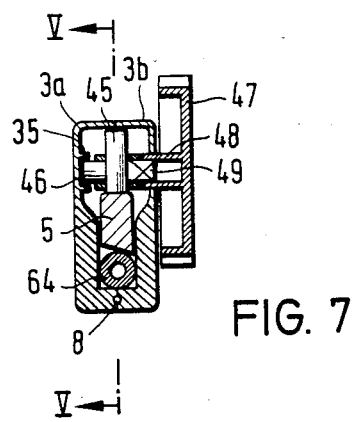
FIG. 7 is a sectional view along line VII—VII of FIG. 5.
Figure 8:
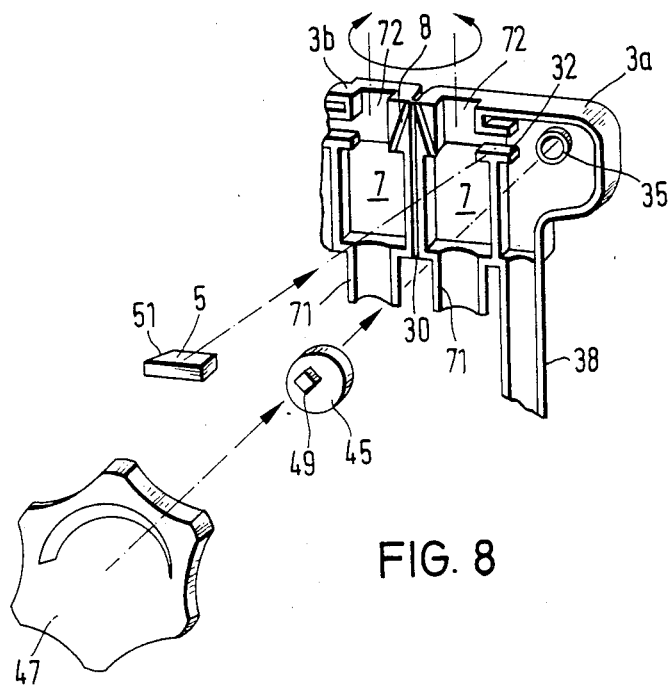
FIG. 8 is an exploded perspective view of the dosing means of FIG. 5, the housing halves being open.

In a closed condition, the housing 3 forms a chamber 7 in which the hose portion 6 is incorporated. The chamber 7, substantially adapted to the outer contour of the hose portion 6, comprises within the region of the thin cylindrical hose portion 63 a neck 71 and within the region of the thin cylindrical hose portion 64 a channel 72 (FIGS. 3 and 4). The annular shoulders 61 and 62 of the hose portion 6 are adjacent to a wall of the chamber 7 thus fixing the position of the hose portion 6. A puncture channel 8 for guiding a needle cannula to chamber 7 extends through the housing 3 at an acute angle relative to its longitudinal axis. This puncture channel 8 ends directly ahead of the annular shoulder 61 which is formed by the stepped thicker part 65 of the hose portion 6.

The pressing element used in the embodiments of the dosing means 1 of FIGS. 1 to 8 is a square-shaped dosing wedge 5 which, at its broad side, is pressing in a straight guide path 32, extending perpendicular to the hose portion on the cylindrical hose section 64 shortly ahead of the annular shoulder 61 of the hose portion 6. The end face 51 of the dosing wedge 5 presses the hose section 64 towards the flat bottom surface of the channel 72. The face 51 extends obliquely to the bottom surface in the cross sectional plane of the hose portion 6. Thus, with the application of the dosing wedge 5, the hose portion will be progressively clamped from the one side.

The dosing wedge 5 is operated by an adjusting device or setting means 4, the return movement being performed by the elastic restoring force of the hose portion 6. As illustrated in FIGS. 1 to 4, the setting means 4 may consist of a threaded spindle 40 disposed in a thread 33 of the housing 3a and actuated by a setting wheel 41. With the advance of the threaded spindle 40, pressure is applied to the dosing wedge 5 which urges against the hose section 64. For example, a hexagonal part 42 of the setting wheel 41 may engage a respective recess 43 inside the threaded spindle 40. The positive connection being disengageable, a removal of the setting wheel 41 is possible to prevent e.g. an inadmissible shifting of the dosing means 1. A hollow cylinder 44 projecting from the setting wheel 41 coaxially with the hexagon 42 and being fitted into a respective hollow-cylindrical recess 34 of the housing portion 3a of housing 3 is intended to guide the setting wheel 41 and to inhibit breaking, by tilting, of the hexagon 42.

In the embodiments of FIGS. 5 to 8, the setting means 4 consists of an eccentric 45 secured to an eccentric shaft 46 which is held by the bearing 35 in the housing 3a, and which receives a key-portion 48 of the setting wheel 47 supported with the former in the housing 3a. The eccentric shaft 46 is connected positively and detachably to the setting wheel 47. That portion 49 which receives the key-portion 48 of the setting wheel 47 is of a square or hexagonal shape. Upon actuating the eccentric shaft 46 by means of the setting wheel 47, the dosing wedge 5 is adjusted subject to the angle position of the eccentric 45, the outer peripheral surface of which is pressing on the dosing wedge 5. Due to the flexibility of the hose portion 6 inside the hose section 64, the dosing wedge 5 is constantly urged against the outer peripheral surface of the eccentric 45. The setting means is also self-locking thus preventing the setting wheel 41 from being moved automatically. The other elements of the dosing means 1 correspond to the preceding embodiment.

Figure 9:
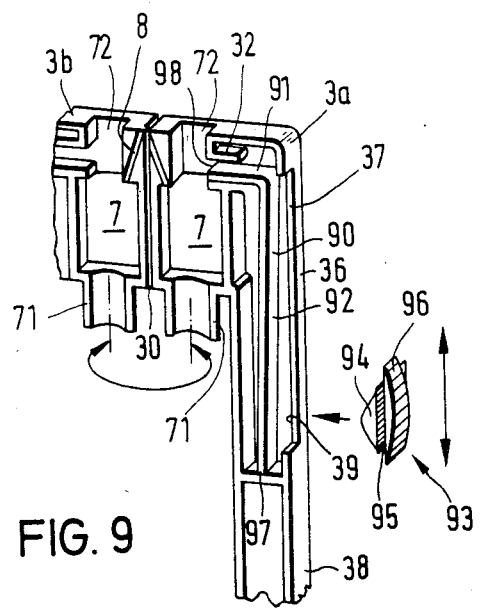
FIG. 9 is a perspective view of a dosing means comprising a lever as an adjusting means, the housing halves being open.

According to the embodiment of FIG. 9, a short leg 91 of an angular lever 90, rather than the dosing wedge 5, presses on the hose portion 6, the lever 90 being hinged unilaterally with its long leg 92 at a pivot point of housing 3a so that the long leg 92 takes an inclined position relative to the housing wall 36 if the hose portion 6 is relaxed. Between the housing wall 36 and the long leg 92, a slide 93 is inserted. Part of the slide extending inside the housing 3 is supported at the housing wall 36 to press on the long leg 92 of lever 90. When moved away from the pivot point 97 of the lever 90, the slide 93 gradually presses like a wedge on the long leg 92 due to the inclination of the lever 90, while the nearly rectangularly bent short leg 91 of the lever 90 increasingly presses on the hose portion 6. The end side 98 of the short leg 91 of the lever acting on the hose portion 6 is chamfered transversely to the hose extension similarly to that of the dosing wedge 5 thus causing the gradual clamping from one side of the hose portion 6 if the lever 90 is swivelled to the closing position. The slide 93 is guided in a slot 37 in the upper housing wall 36, the inside 39 of which is corrugated, to obtain a self-locking of the setting means in association with the corrugated surface 95 of the slide portion 94 inside the housing 3. The upper part 96 of the slide 93 may be also removable in accordance with the setting wheels 41 and 47 of the preceding embodiments so as to avoid an inadmissible actuation of the dosing means by unauthorized persons.

The housing is an injection molding made of one piece, e.g. of polypropylene. All of the illustrated housings are so designed that they contain two elements 3a and 3b (FIGS. 4, 8 and 9) pivotable for example about a film hinge 30. The two housing elements 3a and 3b may be mutually arrested by compression with the aid of snap locks 31a and 31b. Upon the compression of the two housing elements 3a and 3b, the junction cannot be released without being destructive. Both housing members include a handle portion 38 extending in parallel to the fluid line 2 and permitting the singlehanded operation of the setting means 4 in combination with a setting wheel 41 and/or 47 or a slide 93. The outer contour of the setting wheels 41 and 47 or of the slide 93 is shaped so as to allow an easy handling with one thumb while the other fingers of the hand are gripping the handle portion 38 of the housing 3.

Although the above specification refers to a hose portion 6 having a thicker part 65, it is possible to use a normal flexible hose without a thickening, the connection with the pvc fluid line 2 being established by connecting pieces.

The invention being thus described, it will be obvious that the same may be varied in many ways. Such variations are not to be regarded as a departure from the spirit and scope of the present invention, and all such modifications as would be obvious to one skilled in the art are intended to be included within the scope of the following claims.

What is claimed is:

1. A dosing device used in the infusion or transfusion of fluids connected in a flexible fluid line said device comprising a housing, a tubular element comprising an elastomeric material having leading and trailing sections which traverses said housing to interconnect respective ends of said fluid line, said tubular element comprising a thicker portion between said leading and trailing sections thereof, which thicker portion protects against longitudinal displacement of said housing, and a pressing element supported in said housing for compressing said tubular element, said pressing element engaging said tubular element at said leading section of said tubular element outside the region of said thicker portion.

2. A dosing device according to claim 1, wherein said pressing element is directed perpendicular relative to said tubular element 6 the end face of said pressure element which urges against said tubular element being inclined relative to the moving direction of said pressure element.

3. A dosing device according to claim 2, wherein said housing further includes a puncture channel leading to a cavity formed within said thicker portion of said tubular element for introducing a needle cannula.

4. A dosing device according to claim 3, wherein said puncture channel extends at an acute angle relative to a longitudinal axis of said tubular element.

5. A dosing device according to claim 3, wherein said puncture channel ends at an annular shoulder formed at said leading section in said thicker portion of said tubular element.

6. A dosing device according to claim 1, wherein said pressing element is movable via a manually adjustable self-locking setting means.

7. A dosing device according to claim 6, wherein said setting means comprises a threaded spindle supported in said housing.

8. A dosing device according to claim 6, wherein said setting means comprises an eccentric supported at said housing.

9. A dosing device according to claim 6, wherein said setting means comprises a lever pivotable about a pivot point inside said housing and pressing with a free end on said tubular element, a movably positioned slide provided in a slot of one wall of said housing, said slide being operatively associated with said lever, and said lever being inclined relative to said wall containing said slot.

10. A dosing device according to claim 6, wherein said setting means comprises a detachable setting element.

11. A dosing device according to claim 1, wherein said pressing element is movable via a manually adjustable self-locking setting means, which comprises a disc rotatably supported at said housing, said disc having the pivot axis outside of the disc center, urging said pressing element by the circumference of said disc.

* * * * *